United States Patent
Goldberg et al.

(10) Patent No.: US 10,631,743 B2
(45) Date of Patent: Apr. 28, 2020

(54) VIRTUAL REALITY GUIDED MEDITATION WITH BIOFEEDBACK

(71) Applicant: Odyssey Science Innovations, LLC, Lake Oswego, OR (US)

(72) Inventors: Alex Jeffrey Goldberg, Lake Oswego, OR (US); Aaron Serling Goldberg, Portland, OR (US)

(73) Assignee: THE STAYWELL COMPANY, LLC, Yardley, PA (US)

( * ) Notice: Subject to any disclaimer, the term of this patent is extended or adjusted under 35 U.S.C. 154(b) by 349 days.

(21) Appl. No.: 15/162,572

(22) Filed: May 23, 2016

(65) Prior Publication Data
US 2017/0333666 A1    Nov. 23, 2017

(51) Int. Cl.
*A61B 5/024*     (2006.01)
*A61B 5/0205*    (2006.01)
(Continued)

(52) U.S. Cl.
CPC ........ *A61B 5/02438* (2013.01); *A61B 5/0205* (2013.01); *A61B 5/165* (2013.01);
(Continued)

(58) Field of Classification Search
CPC . A61B 5/0482; A61B 5/6801; A61B 5/02438; A61B 5/0205; A61B 5/165; A61B 5/486; A61B 5/7264
See application file for complete search history.

(56) References Cited

U.S. PATENT DOCUMENTS

2009/0269329 A1* 10/2009 Hyde ............... G06F 19/3481
                                                                424/130.1
2009/0271217 A1* 10/2009 Hyde ............... A61K 31/135
                                                                705/3
(Continued)

OTHER PUBLICATIONS

"Virtual Reality Relaxation / Meditation for Oculus Rift DK2: Guided Meditation VR," Cubicle Ninjas, undated, 3 pages, [Online] [Retrieved on May 13, 2016] Retrieved from the Internet<URL:http://guidedmeditationvr.com/>.
(Continued)

*Primary Examiner* — Xuan M Thai
*Assistant Examiner* — Malina D. Blaise
(74) *Attorney, Agent, or Firm* — Fenwick & West LLP

(57) ABSTRACT

A guided meditation system, such as a virtual reality (VR) guided meditation system, provides biofeedback. Wearable devices (e.g., fitness trackers) record information about a physiological state of a user (e.g., heart rate, blood pressure, sleep, and activity data). Performing guided meditation exercises may help users improve their physiological state (e.g., by decreasing a user's heart rate). The VR guided meditation system automatically retrieves physiological state information from wearable devices or third party applications before and/or after a user performs guided meditation exercises. Based on the retrieved information, the VR guided meditation system provides biofeedback related to effects or potential correlations between an exercise and the user's physiological state. In particular, the biofeedback indicates a certain type of meditation, certain VR environment location, or certain meditation duration that is likely to improve the user's physiological state. The VR guided meditation system also can provide recommended exercises to the user.

21 Claims, 7 Drawing Sheets

(51) Int. Cl.
   *A61B 5/00* (2006.01)
   *A61B 5/16* (2006.01)
   *A61B 5/0482* (2006.01)

(52) U.S. Cl.
   CPC ............ *A61B 5/486* (2013.01); *A61B 5/6801* (2013.01); *A61B 5/7264* (2013.01); *A61B 5/0482* (2013.01)

(56) References Cited

U.S. PATENT DOCUMENTS

| | | | | |
|---|---|---|---|---|
| 2012/0183939 | A1* | 7/2012 | Aragones | A63B 24/0006 |
| | | | | 434/247 |
| 2013/0089851 | A1* | 4/2013 | Drane | G09B 5/06 |
| | | | | 434/362 |
| 2013/0211238 | A1* | 8/2013 | DeCharms | A61B 5/4824 |
| | | | | 600/418 |
| 2015/0223731 | A1* | 8/2015 | Sahin | A61B 5/16 |
| | | | | 600/301 |
| 2015/0297109 | A1* | 10/2015 | Garten | A61B 5/04012 |
| | | | | 600/544 |
| 2015/0351655 | A1* | 12/2015 | Coleman | A61B 5/0482 |
| | | | | 600/301 |
| 2016/0005320 | A1* | 1/2016 | deCharms | G09B 5/065 |
| | | | | 434/236 |
| 2016/0077547 | A1* | 3/2016 | Aimone | G06F 3/012 |
| | | | | 345/8 |
| 2017/0162072 | A1* | 6/2017 | Horseman | G09B 19/00 |
| 2017/0188976 | A1* | 7/2017 | Kalra | A61B 5/165 |
| 2017/0189815 | A1* | 7/2017 | Tweedale | A63F 13/79 |

OTHER PUBLICATIONS

"Headspace: The Science Behind Meditation," Headspace Inc., 2016, 7 pages, , [Online] [Retrieved on May 13, 2016] Retrieved from the Internet<URL:https://www.headspace.com/science>.

* cited by examiner

500

```
Receive user information from a client device of the user
including a request for a guided meditation exercise.
510
              │
              ▼
Provide VR environment information associated with the guided
meditation exercise to the client device for the client device to
display a virtual reality environment to the user during a duration
of the guided meditation exercise.
520
              │
              ▼
Receive pre-exercise information about a physiological state of
the user before the user starts the exercise.
530
              │
              ▼
Provide one or more steps of the guided meditation exercise to
the client device.
540
              │
              ▼
Receive post-exercise information about a physiological state of
the user after the user starts the exercise.
550
              │
              ▼
Generate a report based at least in part on statistics on the pre-
exercise information and the post-exercise information.
560
              │
              ▼
Generate a recommended guided meditation exercise based at
least in part on the report.
570
```

FIG. 5

VIRTUAL REALITY GUIDED MEDITATION WITH BIOFEEDBACK

BACKGROUND

1. Field of Art

This disclosure relates generally to the field of guided meditation, and specifically to providing guided meditation to a user in, for example, a virtual reality environment along with biofeedback.

2. Description of the Related Art

Meditation can provide numerous physical and mental benefits. For example, on a physical level, meditation may increase a person's energy level, lower high blood pressure, improve the immune system, and reduce tension-based pain. On a mental level, meditation may, for example, decrease stress and anxiety, increase happiness, improve emotional stability, and achieve peace of mind. People who practice meditation regularly are more likely to experience these benefits. Guided meditation is a form of meditation in which a person follows voice instructions, either live or recorded, guiding the person step-by-step through a meditation exercise.

Meditating outdoors in nature may facilitate improved meditation experiences compared to meditating indoors. Natural environments such as beaches, oceans, forests, waterfalls, and other pleasant settings can help people relax and focus while meditating. However, it may be impractical for people who do not live or work near these natural environments to meditate in natural environments. In addition, current meditation exercises provide no way to measure how the meditation is affecting the physiological condition of the user and what types of meditation might be more effective for the user.

SUMMARY

A guided meditation system, such as a virtual reality (VR) guided meditation system, provides biofeedback. Virtual reality technology can let users view different relaxing environments through a virtual reality system. For example, the virtual environment may be a natural environment located across the world from the location of a user in real life. Wearable devices such as fitness trackers record information about a physiological state of a user, for example, heart rate, blood pressure, sleep, and activity data. Performing guided meditation exercises may help users improve their physiological state, for example, by decreasing a user's heart rate. The VR guided meditation system automatically retrieves or can receive physiological state information from wearable devices or third party applications before, during, and after a user performs guided meditation exercises. Based on the retrieved information, the VR guided meditation system provides biofeedback to the user indicating how the user's physiological state may have changed after the meditation relative to the physiological state before the meditation (e.g., lower heart rate or blood pressure). In particular, the biofeedback may indicate a certain type of meditation, a certain VR environment location, or a certain meditation duration that is likely to improve the user's physiological state. Furthermore, the VR guided meditation system can also provide recommended meditation exercises customized for the user, e.g., recommending the particular meditation exercise that resulted in the lowest heart rate, lowest blood pressure, best sleep patterns, or other affects that suggest that the user is in a more positive physiological state than before the meditation.

According to one embodiment, a method begins with receiving information from a client device of a user requesting a guided meditation exercise. VR environment information associated with the guided meditation exercise is provided to the client device for the client device to display a virtual reality environment perceptible to the user during the duration of the guided meditation exercise. Pre-exercise information about a physiological state of the user is received before the user starts the exercise. Steps of the guided meditation exercise are provided to the client device. Post-exercise information about a physiological state of the user is received after the user starts the exercise. A report is generated based on statistics of the pre-exercise information and the post-exercise information. In some embodiments, a machine learning model is trained to generate recommended guided meditation exercises based on previous guided meditation exercises performed by users.

BRIEF DESCRIPTION OF DRAWINGS

FIG. 5 is a flow chart illustrating a process for providing guided meditation according to one embodiment.

The figures depict embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

I. System Overview

Figure 1:
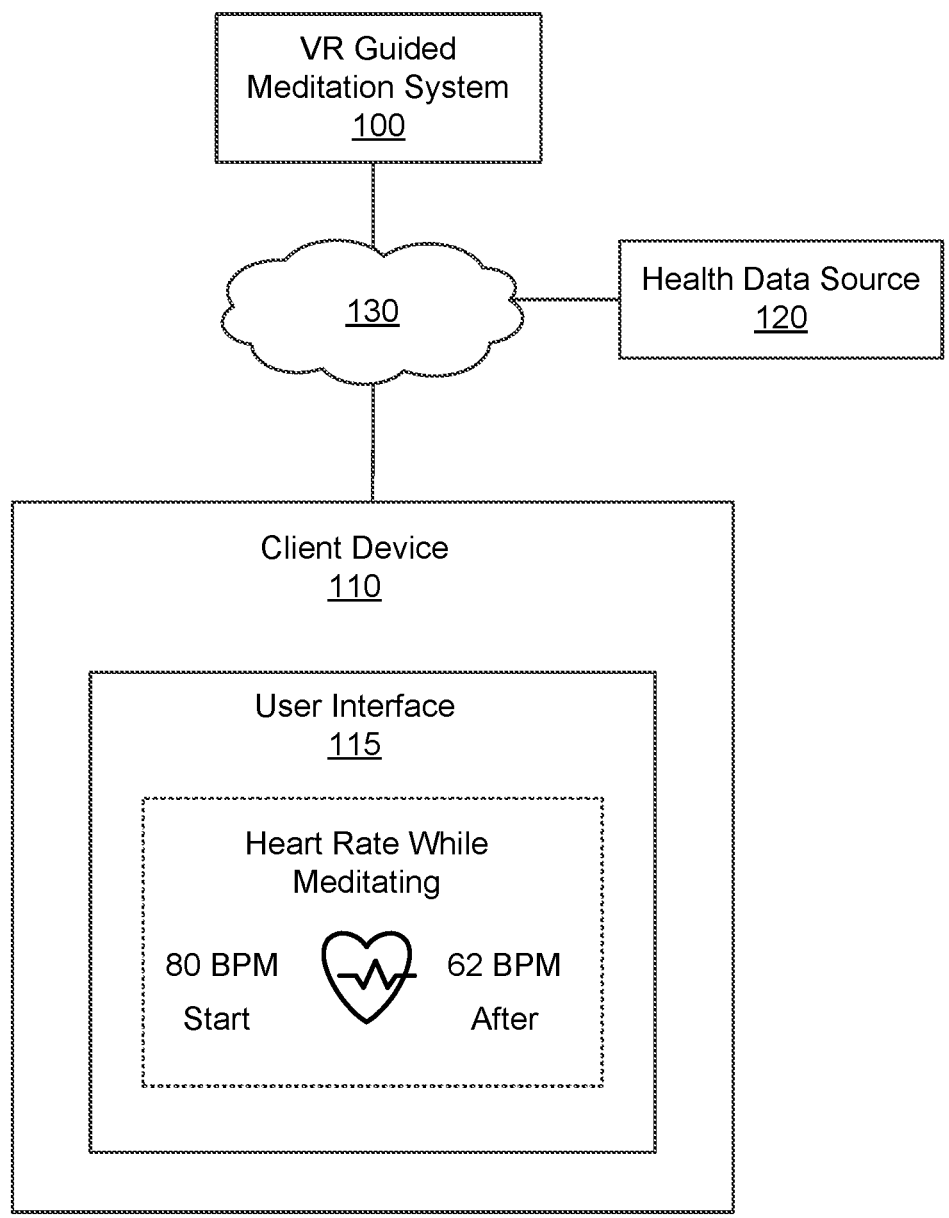
FIG. 1 is a block diagram of a computing environment for guided meditation with a VR guided meditation system according to one embodiment.

FIG. 1 is a block diagram of a computing environment for guided meditation with a VR guided meditation system 100 according to one embodiment. The VR guided meditation system 100, client device 110, and one or more health data sources 120 are each connected to the network 130. A user interacts with the VR guided meditation system 100 via a user interface 115 of the client device 110. Some embodiments of the VR guided meditation system 100 may have additional, fewer, and/or different modules than the ones described herein, and/or have multiple client devices 110 or multiple health data sources 120. The functions can be distributed among the modules in a different manner than described in FIG. 1.

The client device 110 is an electronic device used by a user of the VR guided meditation system 100 to perform functions such as executing software applications, consuming digital content, browsing websites hosted by web servers on the network 130, downloading files, and the like. For example, the client device 110 may be a mobile device, a tablet, a notebook, a desktop computer, or a portable computer. The client device 110 includes interfaces with a display device on which the user may view the user interface 115, webpages, videos and other content. In addition, the client device 110 provides a user interface (UI), such as physical and/or on-screen buttons with which the user may interact with the client device 110 to perform functions such as viewing, selecting, and consuming digital content such as digital medical records, webpages, photos, videos, and other content.

The health data source 120 is a source of physiological state information about a user of the VR guided meditation system 100. The health data source 120 may be an electronic device such as a wearable fitness tracker device, for example, APPLE WATCH®, FITBIT FLEX™, or JAWBONE UP4™. The health data source 120 may also be a third party application, e.g., APPLE® HEALTHKIT, GARMIN®, GOOGLE® FIT, UNDER ARMOUR® MAPMYFITNESS, and STRAVA®. The health data sources 120 can be devices worn on the body or on the clothing of the user, such as a device worn on the wrist, around the neck, around the ankle, on a shirt or a shoe, sensors embedded within a piece of clothing worn by the user, a band around the user's chest, arm, or leg, a headband or head device worn on the user's head, among other options. The physiological state information includes, e.g., the user's heart rate, the user's blood pressure, the user's activity (e.g., number of steps walked, number of miles ran, number of calories burned, etc.), the user's breathing patterns, the user's sleep activity, the user's brain waves, the user's pain response, the user's skin conductance, the user's eye movements, the user's muscle action potentials, the user's temperature, the user's skin electrical activity, or the user's blood flow, among other types of health data.

The network 130 enables communications among network entities such as the client device 110, health data source 120, and VR guided meditation system 100. In one embodiment, the network 130 comprises the Internet and uses standard communications technologies and/or protocols, e.g., BLUETOOTH®, WiFi, ZIGBEE®, clouding computing, cellular connectivity, other air to air, wire to air networks, and mesh network protocols to client devices, gateways, and access points. In another embodiment, the network entities can use custom and/or dedicated data communications technologies.

In one embodiment, the VR guided meditation system 100 receives a request for a VR guided meditation exercise from a user via the client device 110. The request indicates a type of meditation, time duration for meditation, and location for meditation. Based on the request, the VR guided meditation system 100 provides a VR guided meditation exercise to the user via the client device 110. Before the user starts the VR guided meditation exercise, the VR guided meditation system 100 receives physiological state information about the user from the health data source 120, i.e., pre-exercise information. After the user starts the VR guided meditation exercise, the VR guided meditation system 100 again receives physiological state information about the user from the health data source 120, i.e., post-exercise information. In some embodiments, the post-exercise information includes information collected about the user during the meditation exercise or immediately after the meditation exercise, though it can also include information collected a while after the meditation exercise, such as over the next hour or over the rest of the day, or data collected until in the next meditation exercise occurs. The VR guided meditation system 100 provides biofeedback to the user based on the pre-exercise information and the post-exercise information. For example, the biofeedback indicates that the user's heart rate is 80 beats per minute (bpm) before starting the VR guided meditation exercise and that the heart rate lowered to 62 bpm after completing the VR guided meditation exercise. The biofeedback is displayed on the user interface 115 viewed by the user on the client device 110.

Figure 2:
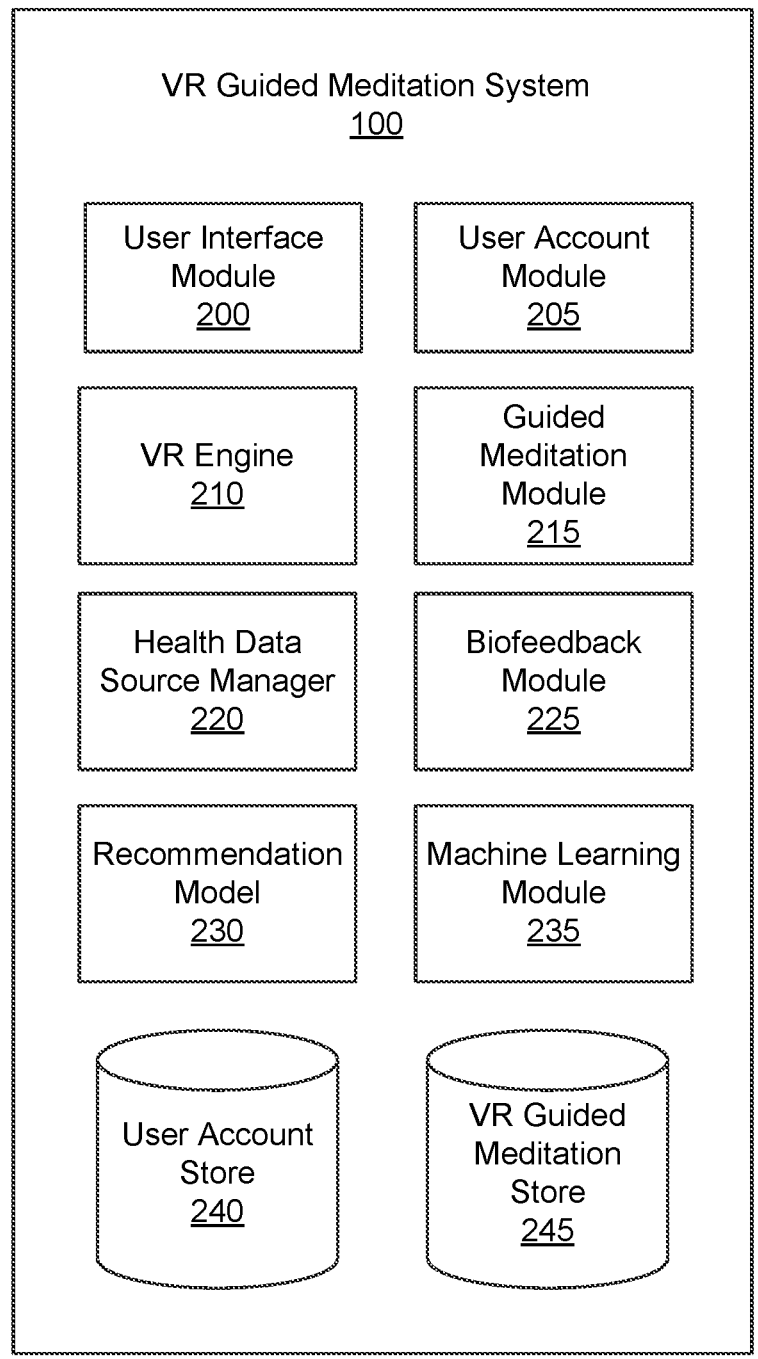
FIG. 2 is a block diagram of the VR guided meditation system within the computing environment of FIG. 1 according to one embodiment.

FIG. 2 is a block diagram of the VR guided meditation system 100 within the computing environment of FIG. 1 according to one embodiment. The VR guided meditation system 100 in FIG. 2 includes a user interface module 200, user account module 205, VR engine 210, guided meditation module 215, health data source manager 220, biofeedback module 225, recommendation model 230, machine learning module 235, user account store 240, and VR guided meditation store 245. In other embodiments, the VR guided meditation system 100 may include additional, fewer, and/or different modules for various applications. Conventional components such as network interfaces, security mechanisms, load balancers, failover servers, management and network operations consoles, and the like are not shown so as to not obscure the details of the system 100. Also, it is noted that the modules may be embodied as hardware, software (which may include firmware), or any combination thereof. For software, it may include program code or code segments. Software is comprised of one or more instructions storable in a computer readable non-transitory storage medium, e.g., a memory or disk, and executable by a processor.

The user interface module 200 generates user interfaces of the VR guided meditation system 100, e.g., user interface 115 shown in FIG. 1. Additional example user interfaces are further described with reference to FIGS. 3A-C. In an embodiment, the user interface module 200 serves web pages, as well as other web-related content, such as Flash, XML, and so forth. The user interface module 200 can provide the functionality of receiving and routing messages and/or information, e.g., between the VR guided meditation system 100, client device 110, as well as other external systems. These messages can be instant messages, queued messages (e.g., email), text and SMS (short message service) messages, or any other suitable messaging technique. The user interface module 200 allows the user to view and/or interact with user interfaces (e.g., user interface 115) of the VR guided meditation system 100 by communicating information between the VR guided meditation system 100 and the client device 110.

The user account module 205 stores user account data associated with users of the VR guided meditation system 100. In an embodiment, the user account data of a user includes information including a name of the user, contact information (e.g., email and phone number) of the user, an employer of the user, information about VR guided meditation exercises that the user has previously started and/or completed, biofeedback associated with the user, recommended VR guided meditation exercises, physiological state information associated with the user, and the like. The VR guided meditation system 100 receives the information from a user via the client device 110, the health data source 120, and/or an external source such as an online database accessible by the VR guided meditation system 100 via the network 130.

The VR engine 210 generates a VR environment associated with a VR guided meditation exercise generated by the guided meditation module 215. In an embodiment, the VR engine 210 extracts VR environment data from the VR guided meditation store 245. The VR environment data may have been previously input, e.g., via a client device 110, to the VR guided meditation store 245 by an expert, e.g., a designer of VR environments. Based on the data, the VR engine 210 generates the VR environment. The VR environment can be a live 360 degree view of an environment. For example, the VR environment is generated based on video captured from a camera with up to a 360 degree view. In an embodiment, the VR environment includes one or more visual and/or audio signals corresponding to a location of the VR environment. For instance, a location of the VR environment is named "garden falls." Accordingly, the one or more visual and/or audio signals corresponding to the "garden falls" location include visual and/or audio signals of waterfalls and garden plants. In particular, a visual signal is a video imagery of a waterfall surrounded by trees and plants with flowers. Further, an audio signal is a sound of water flowing or splashing in the waterfall. Other types of VR environment locations include, e.g., a beach, an island, or a forest, etc., and may be associated with different names such as "paradise beach," "tropical island," or "peaceful forest," etc. The VR engine 210 provides the VR environment to the client device 110, via the user interface module 200, for presentation to the user. In particular, the visual signals (e.g., videos and photos) are presented in a graphical display of the client device 110, e.g., an electronic display of a smartphone. Additionally, the audio signals are presented via audio speakers of the client device 110 and/or another audio playing device (e.g., headphones or external speakers) communicatively coupled to the client device 110.

The guided meditation module 215 generates a VR guided meditation exercise associated with a VR environment generated by the VR engine 210. In an embodiment, the VR engine 210 extracts meditation exercise data from the VR guided meditation store 245. The meditation exercise data may have been previously input, e.g., via a client device, to the VR guided meditation store 245 by an expert, e.g., a meditation instructor or researcher. Based on the meditation exercise data, the VR engine 210 generates the VR guided meditation exercise. In an embodiment, the VR guided meditation exercise includes meditation instructions corresponding to a type of meditation. For instance, a type of meditation is named "breathing." Accordingly, the meditation instructions relate to breathing of a user. For example, the instructions include "keep your breath natural" and "notice where you feel your breath in your body."

In some an embodiments, the VR guided meditation exercise has a time duration, which may be selected by the user or pre-determined. For a VR guided meditation exercise with a short time duration, e.g., 1 minute, the guided meditation module 215 may reduce the number of meditation instructions such that the VR guided meditation exercise can be completed within the shorter time duration. For a VR guided meditation exercise with a long time duration, e.g., 30 minutes, the guided meditation module 215 may increase the number or duration of pauses in between meditation instructions such that the VR guided meditation exercise can be completed within the longer time duration. The guided meditation module 215 provides the meditation instructions to the client device 110, via the user interface module 200, for presentation to the user. In particular, the meditation instructions represented by visual signals (e.g., graphical text of the meditation instructions) are presented in a graphical display of the client device 110, e.g., an electronic display of a smartphone. Additionally, the meditation instructions represented by audio signals (e.g., an audio narration of the meditation instructions) are presented via audio speakers of the client device 110 and/or another audio playing device (e.g., headphones or external speakers) communicatively coupled to the client device 110.

The health data source manager 220 facilitates communication between the VR guided meditation system 100 and the health data source 120 via the network 130. The health data source manager 220 receives, from the user via the client device 110, a request to associate one or more health data sources 120 to an account of the user. Based on the user's account data in the user account store 240, the health data source manager 220 determines whether the user's account is already associated with the health data sources 120. If the user's account is not associated with at least one of the health data sources 120, then the health data source manager 220 informs the user to provide login credentials of the health data sources 120 (that are not already associated with the user's account). For example, the health data source manager 220 generates a user interface for display on the client device 110. The user interface may include text boxes for the user to input the login credentials. The health data source manager 220 receives the input login credentials and authenticates the login credentials, e.g., using an application programming interface (API).

In one embodiment, the heath data sources 120 include a FITBIT® fitness tracker device and an APPLE® HEALTHKIT application. The health data source manager 220 receives login credentials for each of the health data sources 120. The health data source manager 220 provides, via an API, login credentials corresponding to the fitness tracker device to a FITBIT® (third-party) application. If the FITBIT® application authenticates the login credentials, then the health data source manager 220 is authorized to retrieve information from an account of the FITBIT® application associated with the user. Similarly, the health data source manager 220 provides, via an API, login credentials corresponding to the HEALTHKIT application to an APPLE® (third-party) application. If the APPLE® application authenticates the login credentials, then the health data source manager 220 is authorized to retrieve information from an account of the APPLE® application associated with the user. The health data source manager 220 stores input login credentials in the user account store 240 so that the user does not need to provide the login credentials multiple times. Generally, once the VR guided meditation system 100 receives authorization to access information from a health data source 120, the health data source manager 220 can retrieve information about physiological states of users from the health data source 120. For example, the health data source manager 220 retrieves pre-exercise information, post-exercise information, and information while a user is performing a VR guided meditation exercises, i.e., in progress. In some embodiments, the health data source manager 220 retrieves information about a user periodically throughout the day, or at predetermined times (e.g., morning, afternoon, and night). In some embodiments, the health data sources 120 are push systems that provide information to the VR guided meditation system 100, e.g., without requiring the health data source manager 220 to request or retrieve the information. For example, a health data source 120 pushes a user's current heart rate information to the health data source manager 220 once every hour.

The biofeedback module 225 generates biofeedback based on physiological state information about a user of the VR guided meditation system 100. The biofeedback is also based on information about VR guided meditation exercises performed by the user. In one example (shown in user interface 300 in FIG. 3A), the biofeedback indicates a heart rate of the user before starting a VR guided meditation exercise and a heart rate of the user after completing the VR guided meditation exercise. The biofeedback may be represented by statistics or visual elements such as different types of graphs. For instance, the biofeedback includes a graph (e.g., graph 304 shown in FIG. 3A) illustrating the heart rate of a user while the user is meditating. The biofeedback may suggest that performing VR guided meditation exercises helps improve a physiological state of the user. For instance, the heart rate of the user before starting the VR guided meditation exercise is 80 bpm, and the heart rate of the user after completing the VR guided meditation exercise is 62 bpm. Thus, the biofeedback suggests that performing the VR guided meditation exercise helped lower the user's heart rate, which is desirable, e.g., because a lower heart rate indicates that the user is more likely to be less stressed, and thus healthier.

In some embodiments, the biofeedback module 225 generates biofeedback based on demographic information and/or health metrics of the user. The demographic information describes, e.g., the age, gender, or geographical location of the user. The health metrics describe, e.g., the weight, body mass index, blood pressure, or chronic disease condition of the user. Health metrics may also be referred to as body metrics, biometrics, or biological indicators. In one example (shown in the user interface 310 in FIG. 3B), the biofeedback indicates an average heart rate of the user compared to an average heart rate of a population of users within the same age range of the user. In another example, the biofeedback describes a goal for the user based on the user's age. The goal may indicate a target amount of hours that the user should sleep on average each day based on clinical recommendations, e.g., teenagers should sleep 9 hours on average each day.

In some embodiments, the biofeedback module 225 generates a report of a user's biofeedback. The report can provide various data about the user and one or more changes in the user's health metrics before and after a guided meditation exercise, or biofeedback data about the user received before, during, and after the guided meditation exercise. The report can include information about the user and a comparison of the user to a population of other users who have also performed guided meditation exercises. As one example, the report indicates that the user's breathing pace, heart rate, and blood pressure each decreased about 2 minutes into a guided meditation exercise. The report might indicate that the user's weight has decreased within two months of starting guided meditation exercises. The report might include information about the user's sleep patterns indicating that the user is sleeping more peacefully without waking up throughout the night by performing a particular type guided meditation exercise over another type of guided meditation exercise (e.g., "breathing" type meditation appears more correlated with uninterrupted sleep than "body scan" type meditation). The sleep patterns may also show a stronger improvement in the user's sleep patterns relative to those of a population of users performing the same type of meditation exercise.

The user may also share the report with another user, for example, an employer, doctor, or therapist of the user. In an example use case, a user's doctor may prescribe a VR guided meditation exercise as part of a treatment for the user, which may include other types of treatment such as medications or therapies. Based on the report, the user can determine whether the prescribed VR guided meditation exercise appears to have helped improve the user's physiological state or health metrics. The report provided to the doctor may include the user's own data and/or the user's data compared to data of a population of other users who have performed guided meditation exercises in an aggregate report. Another example use case is where a group of users are employees of an employer and participating in a workplace wellness program. The biofeedback module 225 aggregates biofeedback of the group to generate the report. For instance, the biofeedback module 225 reports the average meditation performance of the employees to the employer. In yet another example use case, users may share their biofeedback reports to a health insurance companies or other health care providers.

The biofeedback can indicate trends or changes over time of a physiological state of the user. For example, the average daily heart rate of a user decreases by 10 bpm over the duration of a month. The biofeedback may indicate that the trends or changes appear to be correlated to VR guided meditation exercises, e.g., as the user performs more "breathing" type VR guided meditation exercises, the user's heart rate decreases. As another example, the biofeedback indicates that a user has an average of seven hours of sleep each night during weeks that the user performed at least five VR guided meditation exercises, and an average of five hours of sleep each night during weeks that the user performed less than five VR guided meditation exercises. Thus, the biofeedback indicates that the user's average number of hours of sleep is correlated to the number of VR guided meditation exercises performed by the user during the week. In addition to individual-based biofeedback, the trends or changes (as well as the generated report previously described) can be based on aggregate information from a population of users or a subpopulation of users. The users may be categorized into subpopulations based on demographic data or health metrics of the users. For example, the biofeedback indicates the average change in heart rate during a month for users who are categorized as overweight, average weight, or underweight.

The recommendation model 230 generates meditation exercise recommendations based on information about users of the VR guided meditation system 100. In some embodiments, the recommendation model 230 is a machine learning model. In one use case of the VR guided meditation system 100, a user manually selects a type of meditation exercise (e.g., "body scan," "breathing," or "anxiety"), a VR environment location (e.g., "garden falls," "coastal pond," or "paradise beach") to view while performing the meditation exercise, and/or a duration of meditation (e.g., 2 minutes, 5 minutes, or 10 minutes). In another use case, the user selects a VR guided meditation exercise automatically suggested by the recommendation model 230, which saves the user's time and provides a more engaging user experience because the user does not need to manually select each option for the meditation exercise. Additionally, since the recommendation model 230 is trained based on information specific to a user, the meditation exercise recommendations are customized for the user. Therefore, the meditation exercise recommendations are more likely to help the user improve the user's physiological state. For example, based on previous VR guided meditation exercises performed by the user, the user's biofeedback indicates that the user experiences the greatest decrease in blood pressure when the VR environment of the exercises is a "paradise beach" location. The machine learning module 235 uses the user's biofeedback to update the user's recommendation model 230. Thus, the meditation exercise recommendations suggest that the user perform VR guided meditation exercises while viewing the "paradise beach" location more frequently.

The machine learning module 235 uses machine learning techniques to generate the recommendation model 230. In particular, the machine learning module 235 may generate a model based on optimization of algorithms that analyze information from the user account store 240 (e.g., demographic information about users, information about VR guided meditation exercises performed by users, or biofeedback associated with users). For example, the machine learning module 235 generates a classifier that takes as input a set of VR guided meditation exercises performed by a user and the corresponding biofeedback information. The VR guided meditation exercises are each associated with a different type of VR environment location and the biofeedback information describes the pre-exercise heart rate and post-exercise heart rate of the user associated with each of the VR guided meditation exercises. The classifier outputs which of the VR environment locations corresponds to the greatest decrease in the user's heart rate from pre-exercise to post-exercise. The recommendation model 230 can use the output of the classifier—in addition to the output of other classifiers generated by the machine learning module 235— to generate meditation exercise recommendations for a certain user. In some embodiments, the machine learning module 235 uses other machine learning techniques for generating meditation exercise recommendations, for example, tree-based models, neural networks, information retrieval, or any combination thereof.

In some embodiments, the VR guided meditation system 100 uses multiple recommendation models 230 to generate meditation exercise recommendations for users. For example, the machine learning module 235 may divide users into different subsets of users based on the users' demographic information, e.g., age, gender, geographic location, ethnicity, and/or health metrics, e.g., weight, body mass index, blood pressure, chronic diseases, health condition, and the like. Additionally, the users may be divided based on other types of information such as employers of the users, users who are connected via an online system such as a third-party social networking system. The machine learning module 235 generates one recommendation model 230 for each subset of users, e.g., because different subsets of users may have different types of optimal meditation exercises. For instance, to achieve a 10 bpm decrease (pre-exercise to post-exercise) in heart rate, users in the 50-60 year old range need to meditate on average for 10 minutes, while users in the 20-30 year old range need to meditate on average for 15 minutes. Thus, a recommendation model 230 customized for a subset of users is more likely to provide more effective (i.e., more likely to improve the user's physiological state) meditation exercise recommendations compared to a general recommendation model 230 for an entire set of users.

The machine learning module 235 uses training data sets including features for training the recommendation models 230. The machine learning module 235 generates training data sets based on information retrieved from the user account store 240. In one embodiment, the training data sets are tuples including features, i.e., information describing demographic information about users, information about VR guided meditation exercises performed by users, and/or biofeedback associated with users. In some embodiments, the machine learning module 235 performs online training by retrieving training data sets from a global database of training data accessible over the network 130, e.g., including aggregated information based on a population of users of VR guided meditation systems 100. Further, the machine learning module 235 may upload training data sets to the global database. The training data sets may be organized based on demographic information, e.g., training data sets are categorized based on VR guided meditation exercises performed by teenage users versus VR guided meditation exercises performed by elderly users. Training data sets are further described with reference to FIG. 4.

In some embodiments, the machine learning module 235 periodically retrains recommendation models 230. For example, as a user performs more VR guided meditation exercises over time using the VR guided meditation system 100, the machine learning module 235 generates new training data sets based on the VR guided meditation exercises. The machine learning module 235 may retrain, using the new training data sets, a recommendation model 230 associated with a given user after each VR guided meditation exercise performed by the user. The machine learning module 235 may retrain recommendation models 230 at a rate based on other factors such as, for example, how frequently a user performs VR guided meditation exercises, or the quality of biofeedback associated with a user. For example, the machine learning module 235 retrains recommendation models 230 more frequently for a user if the user performs more meditation exercises compared to the average number of meditation exercises performed (e.g., over a certain period of time) by a population of users. In another example, if the user's heart rate is not decreasing after the user has performed at least a threshold number of meditation exercises recommended by the recommendation model 230, then the machine learning module 235 retrains a recommendation model 230 associated with the user, e.g., using new training data sets from a global database.

II. User Interfaces

Figure 3A:
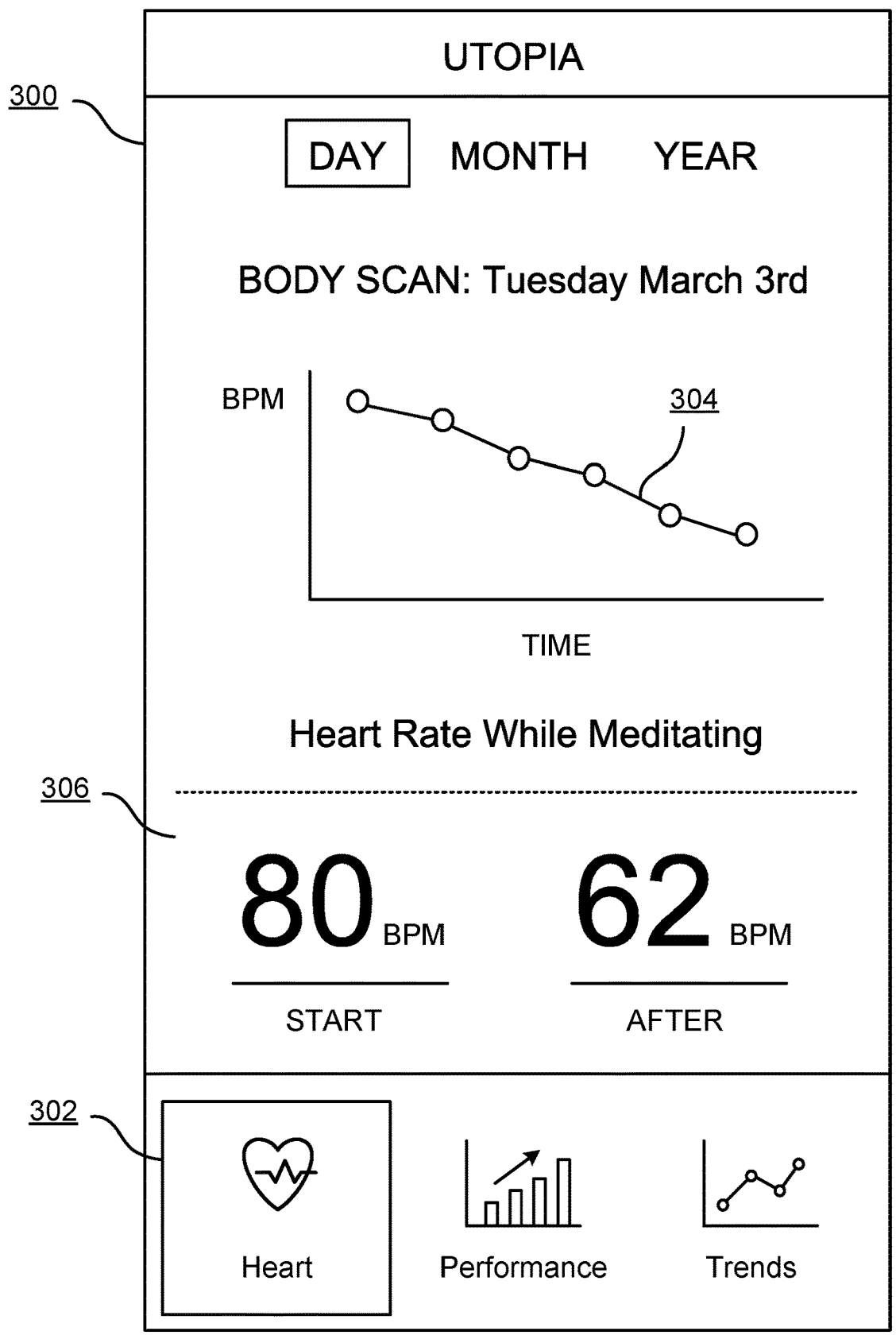
FIG. 3A is a user interface illustrating heart rate biofeedback according to one embodiment.

FIG. 3A is a user interface 300 illustrating heart rate biofeedback according to one embodiment. The user interface 300, e.g., generated by the biofeedback module 225, includes a selection 302 to display heart rate type biofeedback of a user of the VR guided meditation system 100. The user interface 300 also includes a graph 304 and statistics 306 describing a user's heart rate while meditating. In particular, the x-axis of the graph 304 indicates time and the y-axis of the graph 304 indicates the user's heart rate in bpm. In the embodiment shown in FIG. 3A, the graph 304 indicates that user's heart rate gradually decreased over time during a VR guided meditation exercise. Further, the user interface 300 indicates that the graph 304 is associated with a "body scan" type VR guided meditation exercise performed by the user on a given day. In other embodiments, the user interface 300 includes graphs of biofeedback associated with VR guided meditation exercises performed by the user over the duration of a month, a year, or any other duration of time. The statistics 306 indicate that the user's heart rate before starting the VR guided meditation exercise is 80 bpm and that the user's heart rate after starting the VR guided meditation exercise is 62 bpm, e.g., corresponding to the information shown in the graph 304.

Figure 3B:
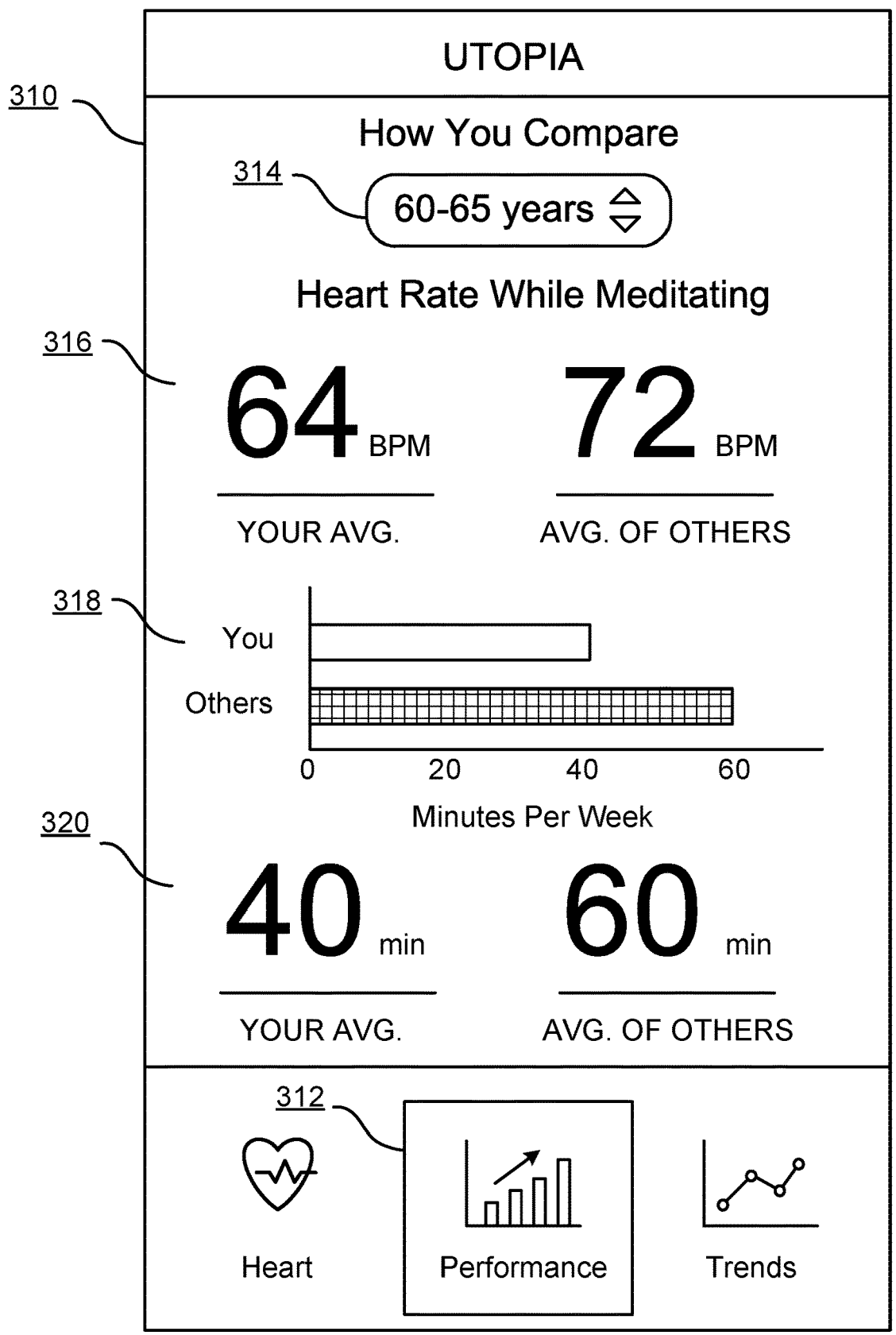
FIG. 3B is a user interface illustrating meditation performance biofeedback according to one embodiment.

FIG. 3B is a user interface illustrating meditation performance biofeedback according to one embodiment. The user interface 320, e.g., generated by the biofeedback module 225, includes a selection 312 to display biofeedback performance of a user of the VR guided meditation system 100. The user interface 300 also includes a selection 314 of an age range of users, statistics 316 describing a user's heart rate while meditating, graph 318, and statistics 320 describing how much time the user meditates. In particular, the selection 314 indicates an age range of 60-65 years old. In other embodiments, the age range may be 0-20 years old, 18-25 years old, 65+ years old, or any other suitable age range. The statistics 316 indicate that the user's heart rate while meditating (i.e., performing VR guided meditation exercises) is 64 bpm on average. The statistics 316 also indicate that the average heart rate for other users in the same (e.g., 60-65 year old) age group while meditating is 72 bpm. Thus, the statistics 316 indicate that the user's biofeedback performance is better than average for the selected age group, e.g., because a lower heart rate is more desirable. The statistics may also be presented as a percentage, indicating the percentage change in the heart rate of the user in comparison to other users.

The graph 318 shows that number of minutes per week that the user meditates on average compared to other users in the selected age group. In particular, the graph 318 indicates that the user performs VR guided meditation exercises for an average of 40 minutes per week and that other users meditate for an average of 60 minutes per week. The statistics 320 indicate the same information as the graph 318. The graph 318 shown in FIG. 3B is a bar graph, though it should be noted that in other embodiments, user interfaces of the VR guided meditation system 100 may include other types of graphs such as line graphs, pie graphs, histograms, scatterplots, and the like, as well as other forms of visual representation of statistics. Additionally, the statistics 316 and 318 indicate average values, though it should be noted that in other embodiments, user interfaces of the VR guided meditation system 100 may include other types of statistics such as standard deviations, confidence intervals, and the like.

Figure 3C:
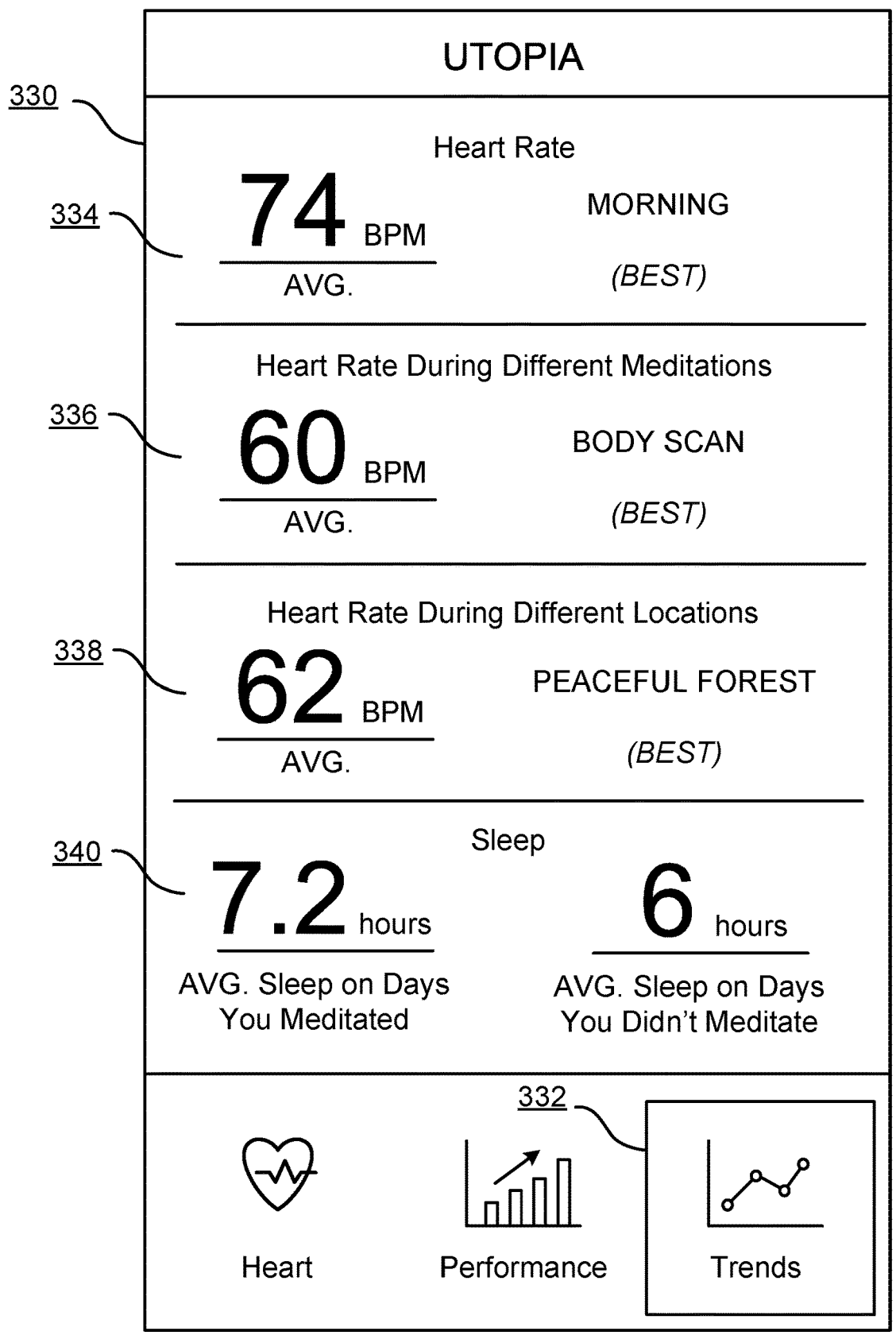
FIG. 3C is a user interface illustrating biofeedback trends according to one embodiment.

FIG. 3C is a user interface illustrating biofeedback trends according to one embodiment. The user interface 330, e.g., generated by the biofeedback module 225, includes a selection 332 to display biofeedback trends of a user of the VR guided meditation system 100. The user interface 330 includes statistics describing the user's biofeedback trends associated with different parameters. In particular, statistic 334 indicates that the user's average heart rate while meditating in the morning is 74 bpm. Since 74 bpm is lower than the user's heart rate while meditating during other times of the day, e.g., afternoon or evening, the statistic 334 also indicates that morning is the best time for the user to meditate. Statistic 336 indicates that the user's average heart rate while performing "body scan" type VR guided meditation exercises is 60 bpm. Since 60 bpm is lower than the user's heart rate while performing other types of VR guided meditation exercises, e.g., "breathing," "anxiety," or "focus," the statistic 336 also indicates that "body scan" is the best type of meditation exercise for the user. Statistic 338 indicates that the user's average heart rate while performing VR guided meditation exercises associated with a "peaceful forest" type VR environment location is 62 bpm. Since 62 bpm is lower than the user's heart rate while performing VR guided meditation exercises associated with other types VR environment locations, e.g., "garden falls," "coastal pond," or "paradise beach," the statistic 338 also indicates that "peaceful forest" is the best type of VR environment location for the user.

The statistic 340 indicates the user's sleep activity biofeedback associated with VR guided meditation exercises performed by the user. In particular, the statistic 340 indicates that the user's average duration of sleep on days that the user meditated is 7.2 hours, and that the user's average duration of sleep on days that the user did not meditate is 6 hours. Thus, the statistic 340 suggests that the user is able to sleep for a longer duration of time on days that the user meditated, which is desirable, e.g., because 7.2 hours is closer to the user's target duration of sleep relative to 6 hours, based on clinical guidelines (e.g., 7-9 hours of sleep per day for adults). In other embodiments, statistics indicate a level of activity of the user on days that the user meditated compared to a level of activity of the user on days that the user did not meditate. For example, the statistics indicate that the user walked an average of 8000 steps on days that the user performed at least one VR guided meditation exercise and that the user walked an average of 5000 steps on days that the user did not meditate.

III. Machine Learning Model

Figure 4:
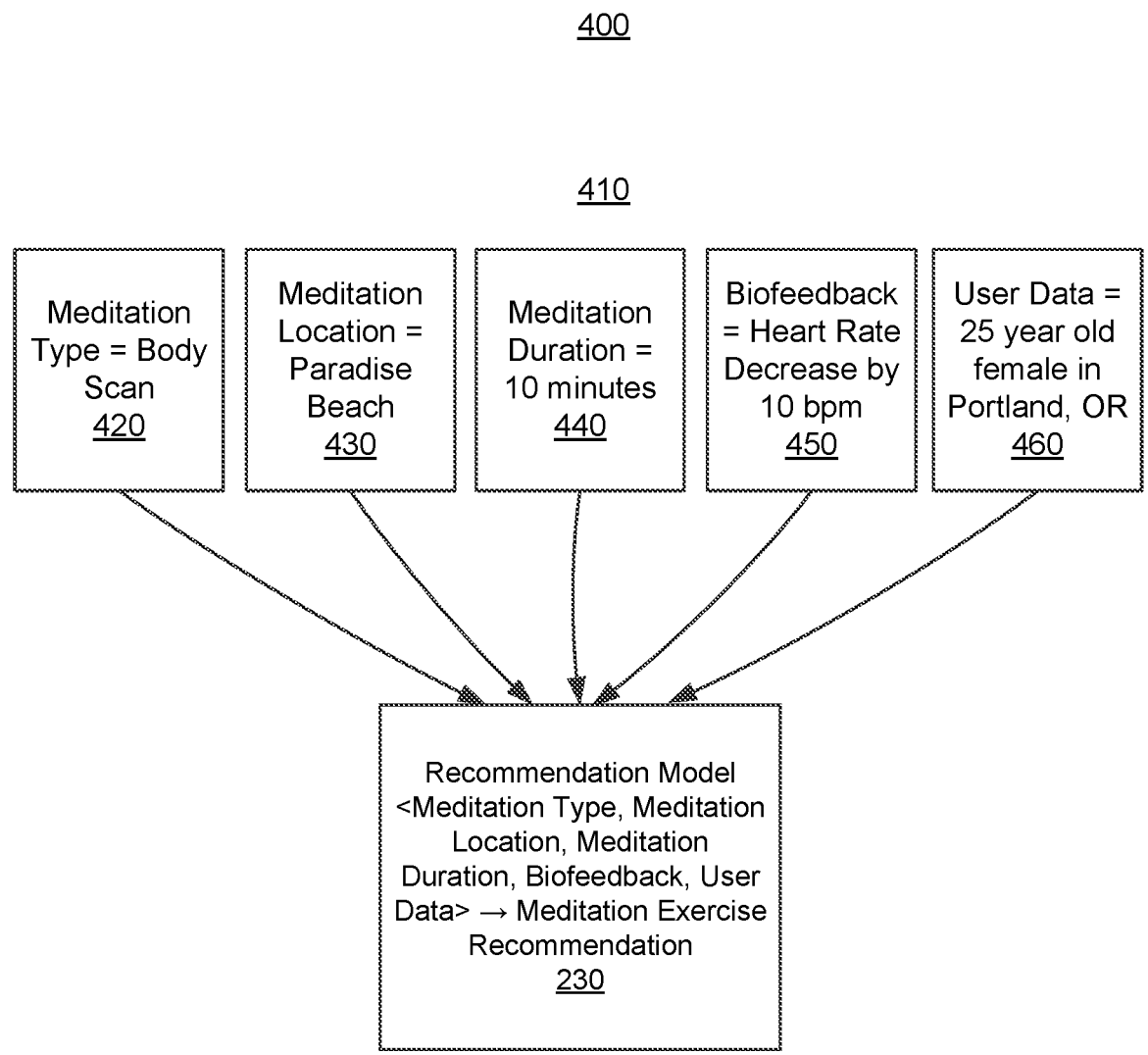
FIG. 4 is a data flow diagram illustrating interactions between data of the VR guided meditation system for training a model for generating meditation exercise recommendations according to one embodiment.

FIG. 4 is a data flow diagram 400 illustrating interactions between data of the VR guided meditation system 100 for training a model for generating meditation exercise recommendations according to one embodiment. In particular, the machine learning module 235 trains the recommendation model 230 using features described by tuples 420, 430, 440, 450, and 460 of a training data set 410. The features are based on information describing users and VR guided meditation exercises performed by users. In one example, a user is a 25 year old female in Portland, Oreg. The user performs a "body scan" type VR guided meditation exercise associated with a "paradise beach" VR environment location for 10 minutes. In addition, the user's post-exercise heart rate is 10 bpm lower than the user's pre-exercise heart rate. Accordingly, tuple 420 indicates the meditation type, "body scan." Tuple 430 indicates the meditation location, "paradise beach." Tuple 440 indicates the meditation duration, "10 minutes." Tuple 450 indicates the biofeedback, "heart rate decrease by 10 bpm." Tuple 460 indicates the user data, "25 year old female in Portland, Oreg."

In the embodiment shown in FIG. 4, the recommendation model 230 takes as input a meditation type, meditation location, meditation duration, biofeedback, and user data. Based on the input, the recommendation model 230 generates a meditation exercise recommendation. Meditation exercise recommendations may recommend that a user perform a certain type of VR guided meditation exercise, perform meditation exercises while viewing a certain VR environment location, perform meditation exercises for a certain time duration (or range of time durations), or any combination thereof. The meditation exercise recommendations may depend on the user data. For example, a meditation exercise recommendation for a 30 year old male is different than a meditation exercise recommendation for a 50 year old female. The training data set 410 includes five tuples, though it should be noted that in other embodiments, the machine learning module 235 uses training data sets including additional, fewer, or different features (e.g., represented by tuples) to train recommendation models 230.

IV. Process Flow

FIG. 5 is a flow chart illustrating a process for providing guided meditation according to one embodiment. In some embodiments, the process 500 is used—for example, by modules of the VR guided meditation system 100—within the computing environment of FIG. 1. The process 500 may include different or additional steps than those described in conjunction with FIG. 5 in some embodiments, or perform steps in different orders than the order described in conjunction with FIG. 5.

The VR guided meditation system 100 receives 510, via the user interface module 200, user information from a client device of the user. The information includes a request for a VR guided meditation exercise and may also include input indicating a type of meditation, a VR environment location, and a duration of meditation. The VR engine 210 provides 520 VR environment information associated with the VR guided meditation exercise to the client device to display a VR environment to the user during the duration of the VR guided meditation exercise. The health data source manager 220 receives 530 pre-exercise information about a physiological state of the user before the user starts the exercise. The guided meditation module 215 provides 540 one or more steps of the VR guided meditation exercise to the client device. The health data source manager 220 receives 550 post-exercise information about a physiological state of the user after the user starts the exercise. The biofeedback module 225 generates 560 a report (e.g., shown in user interfaces 300, 310, and 330 in FIGS. 3A, 3B, and 3C, respectively) based on statistics using the pre-exercise information and the post-exercise information. The recommendation model 230 generates 570 a recommended VR guided meditation exercise based on the report and/or information about the user. The user may select to perform the recommended VR guided meditation exercise.

In some embodiments, the VR guided meditation system 100 provides VR guided meditation exercises and biofeedback to a user without providing a VR environment. For example, the VR guided meditation system 100 provides one or more steps of a VR guided meditation exercise as audio instructions that the user listens to without a virtual reality component, with a visual picture but not presented in a virtual reality environment, with a meditation guided by a live instructor, among other options. In these use cases, the user can perform the VR guided meditation exercise with the user's eyes closed or while looking at an environment other than a VR environment, for example, a real world environment. Thus, the user can receive biofeedback with this guided meditation system in any type of guided meditation environment. Further, the guided meditation system can similarly collect and analyze physiological state data and health metrics, compare the user's meditation performance to those of other users of a population, provide recommendations based on machine learning models associated with meditation exercises, provide reports to the user and/or other parties, etc.

V. Alternative Embodiments

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable non-transitory medium containing computer program code, which can be executed by a computer processor for performing any or all of the steps, operations, or processes described.

Embodiments of the invention may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments of the invention may also relate to a product that is produced by a computing process described herein. Such a product may comprise information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

What is claimed is:

1. A computer-implemented method for providing guided meditation to a user, comprising:
   receiving, at a server from a client device of the user a request for a guided meditation exercise;
   determining a virtual reality environment configured to improve physiological state of the user, the virtual reality environment selected from a plurality of virtual reality environments by a machine learning model at the server, the machine learning model trained using historical exercise information of guided meditation exercises previously performed by other users, the other users having a same characteristic with the user, the historical exercise information captured both before and after the guided meditation exercises;
   in response to the request from the user, providing virtual reality environment information for the guided meditation exercise from the server to the client device for the client device to display the virtual reality environment to the user during a duration of the guided meditation exercise;

receiving, at the server, pre-exercise information captured by a sensor describing a physiological state of the user before the user starts the guided meditation exercise;

providing, with the virtual reality environment displayed on the client device, one or more steps of the guided meditation exercise from the server to the client device;

receiving, at the server, post-exercise information captured by the sensor describing a physiological state of the user after the user starts the guided meditation exercise; and determining, by the machine learning model at the server using the pre-exercise information and the post-exercise information, another virtual reality environment for a subsequent guided meditation exercise for the user.

2. The method of claim 1, wherein the pre-exercise information and the post-exercise information are received from one or more wearable devices configured to record physiological state information of the user, the one or more wearable devices including the sensor.

3. The method of claim 2, wherein the physiological state information includes at least a heart rate of the user.

4. The method of claim 2, wherein the physiological state information includes sleep information of the user, and wherein the machine learning model is further trained using average hours of sleep per day based on the sleep information and whether the user completed at least one guided meditation exercise on a certain day.

5. The method of claim 2, wherein the physiological state information includes an activity level of the user, and wherein the machine learning model is further trained using average steps per day based on the activity level and whether the user completed at least one guided meditation exercise on a certain day.

6. The method of claim 1, wherein the request further includes selections for a type of meditation, a type of virtual reality environment location, and a duration of meditation.

7. A computer-implemented method for providing guided meditation to a user, comprising:

receiving, at a server from a client device of the user a request for a guided meditation exercise;

determining a virtual reality environment configured to improve physiological state of the user, the virtual reality environment selected from a plurality of virtual reality environments by a machine learning model at the server, the machine learning model trained using historical exercise information of guided meditation exercises previously performed by other users having a same characteristic with the user;

in response to the request from the user, providing virtual reality environment information for the guided meditation exercise from the server to the client device for the client device to display the virtual reality environment to the user during a duration of the guided meditation exercise;

receiving, at the server, pre-exercise information captured by a sensor describing a physiological state of the user before the user starts the guided meditation exercise;

providing, with the virtual reality environment displayed on the client device, one or more steps of the guided meditation exercise from the server to the client device;

receiving, at the server, post-exercise information captured by the sensor describing a physiological state of the user after the user starts the guided meditation exercise; and further training the machine learning model using features based at least on the pre-exercise information and the post-exercise information, the machine learning model configured to generate recommended virtual reality environments for subsequent guided meditation exercises.

8. The method of claim 7, wherein the features are further based on a type of meditation, a type of virtual reality environment location, and a duration of meditation.

9. The method of claim 7, wherein the features are further based on information captured by sensors describing physiological states of a population of users performing guided meditation exercises.

10. The method of claim 7, further comprising periodically retraining the machine learning model using features based at least on additional guided meditation exercises performed by the user.

11. A non-transitory computer-readable storage medium storing executable computer program instructions, the computer program instructions comprising code for:

receiving, at a server from a client device of the user a request for a guided meditation exercise;

determining a virtual reality environment configured to improve physiological state of the user, the virtual reality environment selected from a plurality of virtual reality environments by a machine learning model at the server, the machine learning model trained using historical exercise information of guided meditation exercises previously performed by other users, the other users having a same characteristic with the user, the historical exercise information captured both before and after the guided meditation exercises;

in response to the request from the user, providing virtual reality environment information for the guided meditation exercise from the server to the client device for the client device to display the virtual reality environment to the user during a duration of the guided meditation exercise;

receiving, at the server, pre-exercise information captured by a sensor describing a physiological state of the user before the user starts the guided meditation exercise;

providing, with the virtual reality environment displayed on the client device, one or more steps of the guided meditation exercise from the server to the client device;

receiving, at the server, post-exercise information captured by the sensor describing a physiological state of the user after the user starts the guided meditation exercise; and determining, by the machine learning model at the server using the pre-exercise information and the post-exercise information, another virtual reality environment for a subsequent guided meditation exercise for the user.

12. The computer-readable storage medium of claim 11, wherein the pre-exercise information and the post-exercise information are received from one or more wearable devices configured to record physiological state information of the user, the one or more wearable devices including the sensor.

13. The computer-readable storage medium of claim 12, wherein the physiological state information includes at least a heart rate of the user.

14. The computer-readable storage medium of claim 12, wherein the physiological state information includes sleep information of the user, and wherein the machine learning model is further trained using average hours of sleep per day based on the sleep information and whether the user completed at least one guided meditation exercise on a certain day.

15. The computer-readable storage medium of claim 12, wherein the physiological state information includes an activity level of the user, and wherein the machine learning model is further trained using average steps per day based on the activity level and whether the user completed at least one guided meditation exercise on a certain day.

16. The computer-readable storage medium of claim 11, wherein the request further includes selections for a type of meditation, a type of virtual reality environment location, and a duration of meditation.

17. A system comprising:
- a client device of a user, the client device configured to display virtual reality environments;
- a wearable device including a sensor, the sensor configured to capture physiological state information of the user; and
- a server including one or more processors and a non-transitory computer-readable storage medium storing computer instructions executable by the one or more processors to:
  - receive, from the client device, a request for a guided meditation exercise;
  - determine a virtual reality environment configured to improve physiological state of the user, the virtual reality environment selected from a plurality of virtual reality environments by a machine learning model at the server, the machine learning model trained using historical exercise information of guided meditation exercises previously performed by other users, the other users having a same characteristic with the user, the historical exercise information captured both before and after the guided meditation exercises;
  - in response to the request from the user, providing virtual reality environment information for the guided meditation exercise from the server to the client device for the client device to display the virtual reality environment to the user during a duration of the guided meditation exercise;
  - receive, at the server, pre-exercise information captured by the sensor describing a physiological state of the user before the user starts the guided meditation exercise;
  - provide, with the virtual reality environment displayed on the client device, one or more steps of the guided meditation exercise from the server to the client device;
  - receive, at the server, post-exercise information captured by the sensor describing a physiological state of the user after the user starts the guided meditation exercise; and
  - determine, by the machine learning model at the server using the pre-exercise information and the post-exercise information, another virtual reality environment for a subsequent guided meditation exercise for the user.

18. The system of claim 17, wherein the server is further configured to:
- determine that a user account of the user is associated with the wearable device; and
- determine, using login credentials of the user received at the server from the client device, that the server is authorized to receive the pre-exercise information and the post-exercise information captured by the sensor of the wearable device.

19. The system of claim 18, wherein the server receives the pre-exercise information and the post-exercise information from a third party application associated with the sensor responsive to determining that the server is authorized.

20. The computer-implemented method of claim 1, further comprising:
- determining, by the server, that a user account of the user is associated with the sensor; and
- determining, using login credentials of the user received at the server from the client device, that the server is authorized to receive the pre-exercise information and the post-exercise information captured by the sensor.

21. The computer-implemented method of claim 20, wherein the server receives the pre-exercise information and the post-exercise information from a third party application associated with the sensor responsive to determining that the server is authorized.

* * * * *